United States Patent
Wenz et al.

(10) Patent No.: US 6,313,189 B1
(45) Date of Patent: Nov. 6, 2001

(54) BIOLOGICALLY RESORBABLE POLYMERIZATION PRODUCTS MADE OF BINDING AGENT SYSTEMS WHICH CAN BE HARDENED BY RADIATION

(75) Inventors: Robert Wenz, Woellstadt; Berthold Nies, Fraenkisch-Crumbach, both of (DE)

(73) Assignee: Merck Patent Gesellschaft mit beschrankter Haftung, Darmstadt (DE)

(*) Notice: Subject to any disclaimer, the term of this patent is extended or adjusted under 35 U.S.C. 154(b) by 0 days.

(21) Appl. No.: 09/297,587

(22) PCT Filed: Oct. 31, 1997

(86) PCT No.: PCT/EP97/06029

§ 371 Date: May 4, 1999

§ 102(e) Date: May 4, 1999

(87) PCT Pub. No.: WO98/20839

PCT Pub. Date: May 22, 1998

(30) Foreign Application Priority Data

Nov. 13, 1996 (DE) .............................. 196 46 782

(51) Int. Cl.$^7$ ...................................... C08F 2/46
(52) U.S. Cl. .......................... 522/179; 522/76; 522/104; 522/115; 522/171; 522/48; 522/82; 522/908; 523/300; 523/109; 523/113; 523/115; 523/122
(58) Field of Search ................................. 523/109, 115, 523/116, 118, 300, 122; 522/908, 48, 82, 83, 182, 122, 121, 76, 104, 115, 171, 179

(56) References Cited

U.S. PATENT DOCUMENTS

| Re. 35,135 | * | 12/1995 | Sakashita et al. | 522/14 |
|---|---|---|---|---|
| 3,607,848 | | 9/1971 | Stoy et al. | 522/154 |
| 3,819,568 | * | 6/1974 | Taylor et al. | 523/116 |
| 4,244,689 | * | 1/1981 | Ashman | 433/175 |
| 4,327,014 | | 4/1982 | Kawahara et al. | 523/116 |
| 4,437,836 | * | 3/1984 | Schmitz-Josten et al. | 433/199.1 |
| 4,451,235 | * | 5/1984 | Okuda et al. | 433/201.1 |
| 4,500,657 | * | 2/1985 | Kumar | 522/81 |
| 4,579,904 | | 4/1986 | Orlowsa et al. | 524/554 |
| 4,602,076 | | 7/1986 | Ratcliffe et al. | 572/7 |
| 4,626,310 | * | 12/1986 | Ritter | 156/307.3 |
| 4,722,948 | | 2/1988 | Sanderson | 523/115 |
| 4,731,425 | | 3/1988 | Ritter | 526/196 |
| 4,778,834 | * | 10/1988 | Murray | 523/212 |
| 4,801,528 | * | 1/1989 | Bennett | 433/220 |
| 4,936,775 | * | 6/1990 | Bennett | 433/220 |
| 5,147,903 | | 9/1992 | Podszun et al. | 523/115 |
| 5,151,479 | * | 9/1992 | Mukai et al. | 526/277 |
| 5,270,350 | * | 12/1993 | Muller et al. | 523/115 |
| 5,296,513 | | 3/1994 | Ige et al. | 523/115 |
| 5,318,999 | | 6/1994 | Mitra et al. | . |
| 5,380,772 | * | 1/1995 | Hasegawa et al. | 522/14 |
| 5,410,016 | * | 4/1995 | Hubbell et al. | 528/354 |
| 5,444,104 | * | 8/1995 | Waknine | 522/24 |
| 5,461,124 | * | 10/1995 | Ritter et al. | 526/84 |
| 5,512,527 | * | 4/1996 | Ritter | 502/150 |
| 5,538,738 | * | 7/1996 | Ritter et al. | 424/486 |
| 5,626,863 | * | 5/1997 | Hubbell et al. | 424/426 |
| 5,663,214 | * | 9/1997 | Okada | 523/120 |
| 5,679,710 | * | 10/1997 | Davy et al. | 514/547 |
| 5,698,020 | * | 12/1997 | Salz et al. | 106/35 |
| 5,708,051 | | 1/1998 | Erdrich et al. | . |
| 5,925,689 | * | 7/1999 | Orlowski et al. | 522/182 |
| 5,936,006 | * | 8/1999 | Rheinberger et al. | 523/116 |
| 5,952,399 | | 9/1999 | Rentsch | 523/116 |
| 5,969,000 | * | 10/1999 | Yang et al. | 523/116 |
| 5,980,253 | * | 11/1999 | Oxman et al. | 433/228.1 |
| 6,017,973 | * | 1/2000 | Tamura et al. | 522/96 |
| 6,057,383 | * | 5/2000 | Volkel et al. | 523/116 |
| 6,060,582 | * | 5/2000 | Hubbell et al. | 528/435 |

FOREIGN PATENT DOCUMENTS

| 2917037 | 4/1980 | (DE) . |
|---|---|---|
| 0017936 | 10/1980 | (EP) . |
| 0085944 | 8/1983 | (EP) . |
| 0086401 | 8/1983 | (EP) . |
| 0090493 | 10/1983 | (EP) . |
| 0104491 | 4/1984 | (EP) . |

\* cited by examiner

*Primary Examiner*—James J. Seidleck
*Assistant Examiner*—Sanza L. McClendon
(74) *Attorney, Agent, or Firm*—Millen, White, Zelano & Branigan, P.C.

(57) ABSTRACT

Described herein are methods for preparing bioabsorbable polymerization products having interconnecting pore structure by polymerizing compositions containing ethylene glycol- or glycero-oligoester(meth)acrylates monomers and, optionally, other components. The polymerization products are particularly useful for dental lacquers, dental inlays and shaped articles which are bioabsorbable and exhibit an interconnecting pore structure.

12 Claims, No Drawings

BIOLOGICALLY RESORBABLE POLYMERIZATION PRODUCTS MADE OF BINDING AGENT SYSTEMS WHICH CAN BE HARDENED BY RADIATION

The invention relates to a process for the preparation of bioabsorbable polymerization products, characterized in that monomeric compounds essentially comprising compositions of the formula I

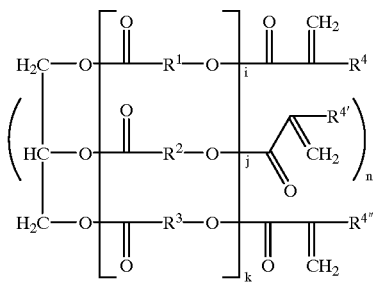

wherein
$R^1$, $R^2$ and $R^3$ in each case independently of one another are —$(CH_2)$—, —$CH(CH_3)$—, —$CH_2$—$CH_2$—, —$CH_2$—$CH_2$—$CH_2$—, —$CH(CH_3)$ —$CH_2$—, —$CH_2$—$CH(CH_3)$—or 1,2-, 1,3- or 1,4-phenylene,
$R^4$, $R^{4'}$ and $R^{4''}$ in each case independently of one another are H or $CH_3$,
i, j and k in each case independently of one another are 0, 1, 2, 3, 4, 5, 6, 7, 8, 9 or 10 and
n is 0 or 1
are polymerized by means of electromagnetic radiation.

The invention also relates to a process characterized in that the compositions of the formula I are polymerized at temperatures between 0 and 80° C.

The invention also relates to a process characterized in that the polymerization of the compositions of the formula I is carried out with the addition of an initiator and/or an accelerator.

The invention also relates to a bioabsorbable polymerization product based on ethylene glycol- and/or glycero-oligoester-(meth) acrylates and obtainable by one of the processes mentioned.

Polymerizable binder systems based on (meth)acrylic acid esters on polyester oligomer chains from hydroxycarboxylic acids are known, for example, from EP 0 085 944 and EP 0 086 401.

Bone substitute materials and implantable drug depots based on acrylate polymers have been known for a long time. Polymer materials based on acrylic and/or methacrylic acid esters have proved suitable here on the basis of their biocompatibility, their outstanding strength properties, their favourable properties regarding the release of embedded pharmaceutical active compounds and, last but not least, on the basis of their processability appropriate for their use.

The invention was based on the object of providing bioabsorbable polymers which are easy to prepare, in particular those which can be used for the preparation of bone and tooth substitute materials.

The use of (meth)acrylic acid esters as monomers for use in dental materials is described, for example, in EP 0 206 074.

Prefabricated shaped articles (inserts) based on ethylenically polymerizable materials are disclosed, for example, in DE 43 39 399.

Other shaped articles having a predetermined pore structure and based on hydroxyapatite are described, for example, in DE 42 05 969.

A process for the preparation of dental fillings from photocuring plastic is described in DE 40 30 168.

Photopolymerizable compositions for dental treatment which are based on phenylene, diphenylene or bridged phenylene are disclosed in DE 21 26 419.

Other photopolymerizable compositions with additions of ketones are described in EP 0 090 493.

It has been found that the compositions of the formula I can be polymerized very readily by irradiation, and the polymer products thus obtained have very valuable properties in processing products such as dental lacquer, dental inlays or porous shaped articles, in addition to their bioabsorbability or biodegradability.

The bioabsorbable polymerization products based on ethylene glycol- and/or glycero-oligoester-(meth)acrylates according to claim 4 can be used in tooth and bone surgery.

The invention accordingly relates to a process for the preparation of bioabsorbable polymerization products, characterized in that monomeric compounds essentially comprising compositions of the formula I are polymerized by means of electromagnetic radiation. The radiation employed for the polymerization lies in the range from 800 nm (near infrared/visible light) up to to $10^{4-4}$ nm (γ-Rays or X-rays). The range of visible and UV light in the range from 800 nm to 1 nm is particularly preferred, and the range from 800 to 50 nm is especially preferred here, while another preferred range comprises wavelengths from 1 to $10^{-4}$ nm.

The ethylene glycol- or glycero-oligoester-(meth) acrylates are preferably formed from 1 mol of ethylene or glycerol, 2 to 10, in particular 2 to 6 mol of monohydroxy-monocarboxylic acid and 2 to 3, preferably 2 mol of methacrylic acid.

Preferred monohydroxy-monocarboxylic acids are glycolic acid, hydroxypropionic acid, hydroxybutyric acid and/or hydroxybenzoic acid, and lactic acid is especially preferred. Preferred compositions of the formula I are consequently the ethylene glycol- and/or glycero-oligolactide-bismethacrylates.

The polymerization is carried out at temperatures of 0 to 80° C., preferably between 10 and 60° C., especially preferably between 20 and 40° C.

Initiators can also be added. Possible suitable initiators are, for example, boron compounds, as described in EP 0 085 944.

The invention furthermore relates to a dental lacquer based on bioabsorbable polymerization products described herein obtainable
a) by mixing the monomeric composition with 0.05 to 4% by weight of camphorquinone,
b) applying the mixture to the tissue to be lacquered or the tooth and
c) polymerizing by means of electromagnetic radiation in the range from 50 to 800 nm.

Because of its chemical build-up, the dental lacquer according to the invention is absorbable. For this reason, it is particularly suitable for treatment of periodontitis, which is characterized by gingival pockets, the formation of colonized plaque, and finally with increasing loss of the periodontal ligament, which represents the connection between the root cement and alveolar socket. As a result of the loss of this tooth-holding apparatus, loosening and loss of the tooth finally occur. The current state of dental treatment comprises debridement of the intermediate space formed between the alveolar socket and tooth root, smoothing of the root surface and sewing-in of a film or membrane (for example Gore membrane) for the purpose of preventing connective tissue growing in from the gingiva in the context of controlled tissue regeneration.

The introduction of the film or membrane and fixing thereof make high demands on the operator. The dental lacquer according to the invention serves to anchor the film or membrane occlusively in the alveolar socket, or the lacquer is introduced into the defect in the context of a spacer for controlled tissue regeneration. To accelerate the regeneration of the tooth-holding apparatus, a rapidly absorbable material, such as, for example, bone sealant, can initially be introduced into the alveolar socket, and the dental lacquer can then be applied to this and polymerized. Calcium salts, antibiotics against bacterial colonization or disinfectants can be mixed into the dental lacquer to improve the formation of root cement by the odontoblasts. Another possibility is to mix in elastase inhibitors. In paradontal diseases, high elastase concentrations originating from polymorphonuclear granulocytes are found in the sulcus fluid. These high elastase concentrations are additionally responsible for the fact that the peridontal attachment apparatus is broken down and the attachment loss continues. Sodium monofluorophosphate, amine fluorides and/or other fluorine donors can furthermore be admixed.

For treatment of exposed necks of teeth, for example, dental lacquer comprising amine fluoride or local anaesthetics is currently applied in order to render the necks of the teeth less sensitive or to harden the necks of the teeth by the release of amine fluorides or other fluorides. However, these dental lacquers have only a short stability on the tooth surface, generally of just a few hours.

The dental lacquer is made to cure faster by mixing in camphorquinone. The amounts to be admixed are preferably between 0.05 and 4% by weight of camphorquinone, in particular between 0.1 and 0.5% by weight.

The polymerization is carried out, for example, by irradiation with visible or UV radiation at wavelengths of 800 to 50 nm, preferably between 500 and 300 nm.

Dental lacquers having different viscosities are obtainable by admixing, for example, glycero-oligoesters and/or glycero-oligoester-(meth)acrylates to ethylene glycol- and/or glycero-oligoester-(meth)acrylates to which camphorquinone has already been added. Preferably, for example, glycero-oligolactides which are formed from 1 mol of glycerol and 6 to 14 mol of lactic acid are admixed to ethylene glycol-oligolactide-bismethacrylates. Glycero-oligo-lactides (1:8 to 1:12) which comprise 1 mol of glycerol and 8 to 12 mol of lactic acid are especially preferred as binders to be admixed.

The amounts to be admixed are preferably between 20 and 60% by weight of glycero-oligolactide, in particular between 30 and 50% by weight.

The amounts to be mixed are preferably between 20 and 60% by weight of glycero-oligolactide, in particular between 30 and 50% by weight.

After the glycero-oligoesters or glycero-oligoester-(meth) acrylates have been mixed in, the system remains photocuring.

The invention furthermore relates to dental inlays based on initially bioabsorbable polymerization products described herein obtainable a) by mixing the monomeric composition with 10 to 80% by weight of hydroxyapatite b) introducing the composition into a dental negative impression and c) polymerizing by means of electromagnetic radiation of less than 10 nm.

A problem which occurs in restorative dentistry when filling dental cavities is the polymerization shrinkage of the materials (inserts), which leads to gaps in the region of the sides of the teeth.

The inlays according to the invention show no such shrinkage.

The inlays are obtainable by mixing ethylene glycol-oligoester-(meth)acrylate with 10 to 80% by weight of hydroxyapatite, preferably with 20 to 70% by weight.

The composition, which is highly viscous before the polymerization, is introduced into a dental impression material (negative impression) and cured by $\Delta$radiation having wavelengths of less than 10 nm, in particular in the range from 1 to $10^{-4}$ nm, preferably in the range from $10^{-1}$ to $10^{-3}$ nm.

The corresponding intensities (radiation densities) of the radiation sources to be used lie at 10 to 60 kGray, preferably at 20 to 50 kGray [rem/cm$^2$].

The bodies formed can be worked mechanically by sawing or drilling. The inlays thus obtained can then be introduced into the prepared tooth and glued, for example by using a bone adhesive comprising, for example, ethylene glycol-oligolactide-bismethacrylate and an initiator.

Embedding experiments on the inlays according to the invention over 6 months at 60° C. show that the material absorbs no water. No loss in weight such as could arise due to degradation is to be detected.

The invention furthermore relates to implantable shaped articles having an interconnecting pore system which are based on bioabsorbable polymerization products describe herein obtainable a) by introducing the monomeric composition into a porous matrix and b) polymerizing by means of electromagnetic radiation of less than 10 nm.

The forms according to the invention are most suitable as bone substitute material having a spacer function, since the trabeculae which form the pore system can be used as guide tracks by the regenerated bone. After a certain time, the polymer is degraded completely, so that only regenerated bone remains, that can then adapt to the corresponding stress directions of the bone to the optimum.

The shaped articles having an interconnecting pore system are produced by introducing matrices, such as, for example, cubes of sugar, into a silicone mold and then impregnating these with the monomeric ethylene glycol-and/or glycero-oligoester-(meth)acrylate. The monomer is polymerized by irradiation with γ-radiation.

γ-radiation having wavelengths of less than 10 nm, in particular in the range from 1 to $10^{-4}$ nm, preferably in the range from $10^{-1}$ to $10^{-3}$ nm, is used. The corresponding radiation densities of the radiation sources to be used lie at 10 to 60 kGray, preferably at 20 to 50 kGray [rem/cm $^2$].

The polymerized cubes of sugar can then be worked for further shaping, or the sugar can then be dissolved out by treatment with water or alcohol.

The invention furthermore relates to the use of bioabsorbable polymerization products describe herein for the preparation of dental lacquers, dental inlays and/or implantable shaped articles.

EXAMPLE 1

50 ml of ethylene glycol-oligolactide-bismethacrylate is mixed with 1% camphorquinone in the absence of light for 20 minutes, while stirring, and the mixture is transferred to a brown glass bottle. The mixture is applied to the tooth and cured with a light stylus, for example from Kulzer, Translux EC, 200 watt, for 2×30 seconds.

The polymer layer formed on the tooth surface is very firm and mechanically stable to abrasion.

EXAMPLE 2

More highly viscous to plastically deformable "dental lacquer" systems are suitable for periodontitis treatment on the beagle. 40% by weight of glycero-oligolactide (1:8), which has been heated beforehand to 50° C., is added to and mixed with the mixture prepared in Example 1 in a kneader.

After application of the dental lacquer, this is cured with a light stylus, Translux EC, 200 watt for 2×40 seconds.

EXAMPLE 3

Mixing 30% by weight of hydroxyapatite into ethylene glycol-oligolactide-bismethacrylate (1:8) gives a highly viscous, solid-porous composition. This is introduced into a negative impression and polymerized by γ-radiation at 25–50 kGy.

EXAMPLE 4

A cube of sugar is introduced into a silicone mold which is constructed such that the edge surfaces of the cube of sugar are enclosed by the silicone on all sides, but the upper side and underneath are left open. By applying a vacuum to the underneath of the silicone mold, after application of 5 ml of ethylene glycol-oligolactide-bismethacrylate to the upper side of the cube of sugar, this is sucked in and through the sugar. The cube of sugar loaded in this way can be stored at 0 to 4° C. Polymerization is carried out by irradiating the material at 25 kGy.

The loading technique can also be modified such that the cube of sugar enclosed by the silicone mold is first loaded with 3 ml of ethylene glycol-oligolactide-bismethacrylate, heated at 60° C., which contains 8% by weight of 9-BBN (borabicyclononane). 5 ml of ethylene glycol-oligolactide-bismethacrylate are then sucked through.

Another loading possibility comprises placing several cubes of sugar in an excess of adhesive monomers in a desiccator and applying a vacuum.

The polymerized cubes of sugar were tested for compressive strength using an Instron testing machine. Shaped articles from which the sugar matrix was not dissolved out by water or alcohol showed compressive strength of 30 mpa, and in the case of shaped articles with the matrix dissolved out, the compressive strength was 3 mpa.

What is claimed is:

1. A process for the preparation of an implantable shaped article comprised of a bioabsorbable polymerization product having an interconnecting pore system which comprises polymerizing a composition contained in a porous matrix in the form of the shaped article by means of electromagnetic radiation of less than 10 nm and dissolving away the porous matrix to provide the shaped article of a bioabsorbable polymerization product having an interconnecting pore system, said composition comprising 10 to 80% by weight of hydroxyapatite and at least one monomeric compound of the formula I

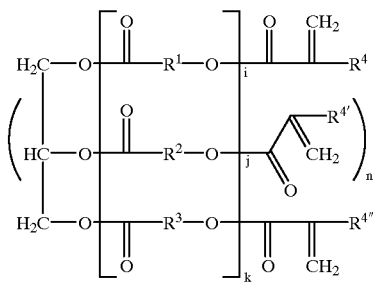

wherein
$R^1$, $R^2$ and $R^3$ in each case independently of one another are —$(CH_2)$—, —$CH(CH_3)$—, —$CH_2$—$CH_2$—, —$CH_2$—$CH_2$—$CH_2$—, —$CH(CH_3)$—$CH_2$—, —$CH_2$—$CH(CH_3)$—or 1,2-, 1,3- or 1,4-phenylene,
$R^4$, $R^{4'}$ and $R^{4''}$ in each case independently of one another are H or $CH_3$,
i, j and k in each case independently of one another are 0, 1, 2, 3, 4, 5, 6, 7, 8, 9 or 10, provided that i, j and k are not simultaneously 0,
n is 0 or 1.

2. A process according to claim 1, wherein the compositions having at least one monomeric compound of the formula I are polymerized at a temperature of from 0 to 80° C.

3. A process according to claim 1, wherein the polymerization of the compositions having at least one monomeric compound of the formula I is carried out with the addition of an initiator and/or an accelerator.

4. An implantable shaped article comprised of a bioabsorbable polymerization product having an interconnecting pore system prepared by the process of claim 1.

5. The polymerization product of claim 4, wherein the product is an implantable shaped article.

6. The process of claim 1, wherein the sum of i, j and k is from 2 to 10.

7. The product of claim 4, wherein the sum of i, j and k is from 2 to 10.

8. The process of claim 1, wherein at least one of $R^1$, $R^2$ and $R^3$ is —$CH(CH_3)$—from lactic acid.

9. The product of claim 4, wherein at least one of $R^1$, $R^2$ and $R^3$ is —$CH(CH_3)$—from lactic acid.

10. The process of claim 1, wherein the polymerization is carried out at a temperature of from 10 to 60° C.

11. The process of claim 1, wherein the electromagnetic radiation for polymerizing is from a radiation source having an intensity from 10 to 60 KGray.

12. The process of claim 1, wherein the porous matrix is comprised of sugar.

* * * * *